United States Patent [19]

Finke et al.

[11] 4,045,480
[45] Aug. 30, 1977

[54] PROCESS FOR PREPARING 1,2-OXA-PHOSPHOLANES

[75] Inventors: Manfred Finke, Fischbach, Taunus; Hans-Jerg Kleiner, Kronberg, Taunus; Elmar Lohmar, Rodenkirchen, all of Germany

[73] Assignee: Hoechst Aktiengesellschaft, Frankfurt am Main, Germany

[21] Appl. No.: 695,126

[22] Filed: June 11, 1976

[30] Foreign Application Priority Data

June 14, 1975 Germany .................... 2526689

[51] Int. Cl.$^2$ ............................................. C07F 9/30
[52] U.S. Cl. ............................. 260/545 P; 260/544 Y
[58] Field of Search ....................... 260/545 P

[56] References Cited

U.S. PATENT DOCUMENTS 2,268,157  12/1941  Marvel ................. 260/545 P X

OTHER PUBLICATIONS

Chajrullin et al., Z. Obsc. Chim., vol. 37, (1967), p. 710.
Chajrullin et al., Z. Obsc. Chim., vol. 38, (1968), p. 288.

*Primary Examiner*—Richard L. Raymond
*Attorney, Agent, or Firm*—Curtis, Morris & Safford

[57] ABSTRACT

Preparation of 2,5-dioxo-1,2-oxa-phospholanes of the formula (I)

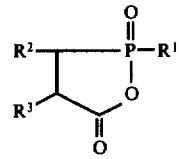

wherein R$^1$ represents an optionally substituted alkyl having up to 18 carbon atoms, a cycloalkyl radical having up to 8 carbon atoms, an alkylene radical having up to 8 carbon atoms, an aryl radical having up to 14 carbon atoms which may be substituted by lower alkyl groups, lower alkoxy groups, halogen or by amino groups alkylated or dialkylated by lower alkyl groups, or an aralkyl radical having up to 15 carbon atoms which may be substituted in an analogous manner as the aryl radical, R$^2$ represents a lower alkyl radical or hydrogen and R$^3$ represents an alkyl radical having up to 6 carbon atoms, a phenyl radical which may be substituted by halogen or by lower alkyl groups, a benzyl radical or hydrogen, by reacting 2-halogenoformylethylphosphonic acid halides of the formula (II)

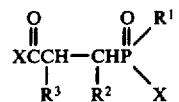

wherein R$^1$, R$^2$ and R$^3$ are defined as in formula (I) and X represents chlorine or bromine, with approximately an equimolar quantity of water or one phosphinic-carboxylic acid of the formula (II), wherein both radicals X represent OH-groups.

11 Claims, No Drawings

PROCESS FOR PREPARING 1,2-OXA-PHOSPHOLANES

It is already known that 2-chloroformylethylphosphinic acid chlorides which are readily obtainable from alkyldichlorophosphines and carboxylic acids unsaturated in $\alpha,\beta$-position may be cyclized with acetanhydride to form 2,5-dioxo-1,2-oxaphospholanes, whereby acetylchloride is obtained as by-product. According to this process 2-methyl- or 2,4-dimethyl-2,5-dioxo-1,2-oxaphospholanes may be obtained from the corresponding chloroformalkylphosphinic acid chlorides in a yield of 84.3 or 78.6%. Calculated on methyldichlorophosphine reacting with acrylic acid or methacrylic acid to yield the corresponding 2-chloroformylalkylmethylphosphinic acid chlorides, 2-methyl- or 2,4-dimethyl-2,5-dioxo-1,2-oxaphospholanes is obtained in a total yield of 67.7 or 60,7% (Cf, V.K. Chajrullin, I.I. Sobcuk and A.N. Pudovik, Z.obsc.chim. 37, 710 (1967), V.K. Chajrullin.R.M. Kondrat'eva and A.N. Pudovik, Z.obsc.chim. 38, 288 (1968)

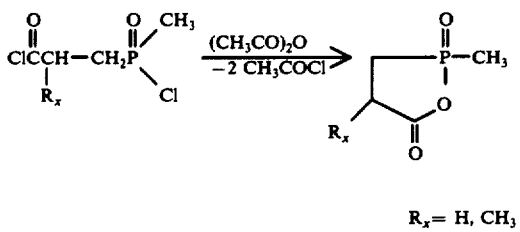

$R_x$= H, CH$_3$

This process has the disadvantage that the crude 2,5-dioxo-1,2-oxaphospholanes are contaminated by rather great quantities of acetanhydride, which may only be split off incompletely even under reduced pressure and leads to discolorations of the crude products at temperatures above 130° C. A high vacuum distillation is indispensable for purifying the 2,5-dioxo-1,2-oxa-phospholanes obtained according to said process.

It has now been found that 2,5-dioxo-1,2-oxaphospholanes of the formula (I)

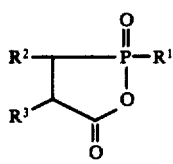

(I)

wherein
R$^1$ represents an alkyl radical having up to 18, preferably 1 to 12, especially 1 to 4 carbon atoms, optionally substituted by halogen, especially by chlorine, preferably up to three times, especially one time, a cycloalkyl radical having up to 8 carbon atoms, especially cyclopentyl, cyclohexyl, an alkenyl radical having up to 8 carbon atoms, especially vinyl and allyl, an aryl radical having up to 14 carbon atoms, especially phenyl, which may be substituted by lower alkyl groups having up to 4 carbon atoms, lower alkoxy groups having up to 4 carbon atoms, halogen or amino groups alkylated or dialkylated by lower alkyl groups having up to 4 carbon atoms, preferably up to twice, or an aralkyl radical having up to 15 carbon atoms optionally substituted in an analogous manner as the aryl radical, especially benzyl R$^2$ represents an alkyl radical having up to 4 carbon atoms preferably methyl or hydrogen and R$^3$ represents an alkyl radical having up to 6 carbon atoms, especially methyl, a phenyl radical optionally substituted by halogen, preferably chlorine or lower alkyl groups having up to 4 carbon atoms, preferably methyl, up to three times; preferably one or two tines, a benzyl radical or hydrogen, at least one of the radicals R$^2$ and R$^3$ representing preferably a hydrogen atom, may be obtained by reacting 2-halogenoformylethylphosphinic acid halides of the formula (II)

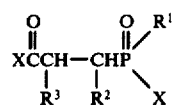

(II)

wherein R$^1$, R$^2$ and R$^3$ are defined as in formula (I) and X represents chlorine or bromine, preferably chlorine, with approximately an equimolar quantity of water or a phosphiniccarboxylic acid of the formula (II) wherein both radicals X represent OH groups.

When using phosphinic-carboxylic acids such having identical radicals R$^1$, R$^2$ and R$^3$ as defined in formula (II) are preferred. Mixtures of phospholanes may also be obtained by varying these radicals.

It is surprising that 2-halogenoformylethylphosphinic acid halides react with equimolar quantities of water or 2-carboxyethylphosphinic acids to yield 2,5-dioxo-1,2-oxaphospholanes as it was to be expected that a polycondensation to yield polymer anhydride structures would occur, at least partically, instead of this cyclization. When condensing terephthalic acid, for example, with terephthalic acid chloride at a temperature from 200° to 300° C, a polyterephthalic acid anhydride is obtained (Cf. Houben-Weyl Methoden der organischen Chemie, Volume XIV/2, page 361, published by Georg Thieme Verlag, Stuttgart, 1963). The reaction according to the invention is moreover surprising owing to the fact that it could be demonstrated that 2-carboxyethylmethylphosphinic acid does not show a cyclization reaction under condensation conditions, even at a temperature above 190° C and under a pressure of 0.05 mmHg, but is converted into phosphinic-carboxylic acid anhydrides while water is split off, anhydrides which are not identical with 2-methyl-2,5-dioxo-1,2-oxa-phospholane according to their spectroscopic data.

Suitable starting compounds for the reaction of the invention are 2-halogenoformylalkylphosphinic acid halides such as:

2-chloroformylethyl-methyl-phosphinic acid chloride
2-chloroformylethyl-ethyl-phosphinic acid chloride,
2-chloroformylethyl-propyl-phosphinic acid chloride,
2-chloroformylethyl-butyl-phosphinic acid chloride,
2-chloroformethyl-hexyl-phosphinic acid chloride,
2-chloroformylethyl-octyl-phosphinic acid chloride,
2-chloroformylethyl-dodecyl-phosphinic acid chloride,
2-chloroformylethyl-vinyl-phosphinic acid chloride,
2-chloroformylethyl-allyl-phosphinic acid chloride,
2-chloroformylethyl-benzyl-phosphinic acid chloride, 2-chloroformylethyl-phenyl-phosphinic acid chloride,
2-chloroformylethyl-p-chlorophenyl-phosphinic acid chloride,
2-chloroformylethyl-cyclohexyl-phosphinic acid chloride,
(2-chloroformyl-1-methyl-ethyl)-methyl-phosphinic acid chloride, (2-chloroformyl-1-methyl-ethyl)-ethyl-phosphonic acid chloride,
(2-chloroformyl-1-methyl-ethyl)-propyl-phosphinic acid chloride,
(2-chloroformyl-1-methyl-ethyl)-vinyl-phosphinic acid chloride,
(2-chloroformyl-1-methyl-ethyl)-phenyl-phosphinic acid chloride,
(2-chloroformyl-1-phenyl-ethyl)-methyl-phosphinic acid chloride,
(2-chloroformyl-2-methyl-ethyl)-methyl-phosphinic acid chloride,
as well as the corresponding 2-carboxyethyl-phosphinic acid. dibromides.

The halogenoformylethylphosphinic acid halides may be readily obtained from the corresponding alkyl-dihalogenophosphines and carboxylic acids unsaturated in αβ-position in an analogous manner to Russian Pat. No. 173,763.

The process according to the invention is advantageously carried out in the following manner: Approximately the equimolar quantity of water or a 2-carboxyethylphosphinic acid as obtained for example by hydrolysis of a corresponding dihalide is reacted with the 2-halogenoformylethylphosphinic acid halides. The water may be added to the phosphine-carboxylic acid dichlorides in undiluted form or dissolved in ethers, for example dioxane, tetrahydrofurane or 1,2-dimethoxyethane or in the form of steam. It is also possible to introduce the 2-halogenoformylethylphosphinic acid halides dropwise into a mixture of water and an inert solvent miscible with water, for example dioxane or tetrahydrofurane. The phosphinic-carboxylic acid may be added in a solid or molten state or dissolved in an ether, for example dioxane, tetrahydrofurane or 1,2- dimethoxyethane. It is likewise possible to introduce the 2-carboxyethylphosphinic-acid dichlorides dropwise into a molten mass or a solution of the corresponding phosphinic-carboxylic acids.

The process may also be performed continuously.

The reaction temperature should be in the range from about −20° to +200° C, preferably from 0° to 160° C, especially from +20° to +130° C. It is not necessary to maintain the temperature at a constant level during the reaction, by outside cooling. It may even be advantageous, when operating without a solvent, to let the temperature raise up to the melting point of the final product in the measure as the reaction progresses, in order to keep the viscosity of the reaction mixture at a low level.

Hydrogen halide formed in the reaction may be rapidly driven off from the reaction solution for example by injecting an inert gas, for example nitrogen. The residual quantities of hydrogen halide may be removed subsequently in a water jet vacuum, for example at a temperature from +50° to +200° C. When operating in solvents it is also possible to catch the hydrogen halide formed by means of an acid acceptor, for example tertiary amines.

Suitable solvents for the reaction according to the invention are: dioxane, tetrahydrofurane, diisopropyl ether, din-butyl ether, methylene chloride, 1,2-dichloroethane, 1,2-dichloropropane, chloroforme, carbon tetrachloride, benzene, toluene, xylene, chlorobenzene, o-dichlorobenzene, petroleum ethers as well as mixtures of these solvents.

The reaction time generally goes from 1 to 6 hours.

Already as crude products the 2,5-dioxo-1,2-oxaphospholanes prepared according to the process of the invention have a good quality of color and the purity required for using them on an industrial scale. The further purification may be carried out by recrystallization from inert solvents, for example dioxane, acetone, chloroforme, 1,2-dichloroethane, 1,2-dichloropropane or from mixtures of these solvents. The 2,5-dioxo-1,2-oxaphospholanes of low molecular weight may be readily purified by distillation under reduced pressure, especially by distillation in a thin-layer evaporator.

The preparation of the 2,5-dioxo-1,2-oxa-phospholanes according to the process of the invention signifies a considerable technical progress, as there are only required as reagents for the cyclization of the 2-halogenoformylethylphosphinic acid halides, which may also be directly used in the form of crude products, water or the phosphinic-carboxylic acids corresponding to the phosphinic-carboxylic acid dihalides, which may be readily prepared from the latters by hydrolysis. The complicated elimination of foreign substances may be dispensed with as these reagents are consumed practically quantitatively in the course of the reaction.

The 2,5-dioxo-1,2-oxa-phospholanes prepared according to the present invention already have a good quality of color and a high purity as crude products so that the phospholanes may be directly used in this state for a series of applications. The yields of 2,5-dioxo-1,2-oxa-phospholanes, calculated on alkyl or aryl-dihalogenophosphines, are in the range of about 85 to 100% of the theory.

2,5-dioxo-1,2-oxa-phospholanes are good flame-proofing agents, which may be used for the preparation of flame resistant linear polyesters. They are moreover valuable intermediates, which may be processed for example to flame-proofing agents.

The following examples illustrate the invention.

EXAMPLE 1

Preparation of 2-methyl-2,5-dioxo-1,2-oxa-phospholane from Methyldichlorophosphine, Acrylic Acid and 2-carboxyethylmethylphosphinic Acid 585 g of methyldichlorophosphine containing 1.4% of $PCl_3$ was introduced into a 2 liter flask provided with a stirrer, a thermometer, a reflux condenser, a drip funnel and a delivery nozzle for $N_2$ and heated to room temperature (576.8 g of $CH_3PCl_2$, 4.94 mols). 365 g of a acrylic acid (5.07 mols) were added dropwise to $CH_3PCl_2$ through the drip funnel while stirring and passing over a weak $N_2$ current in such a manner that the reaction was initiated by a slow addition (increase of the temperature of the contents of the flask to about 40° C) and that the reaction heat was dissipated while cooling the wall of the flask by means of an ice/$H_2O$ bath and rapidly adding such that a temperature of 60° C was maintained in the flask. The addition of acrylic acid was terminated after 1 hour and 20 minutes. The reaction product obtained was a colorless molten mass of 2-chloroformylethylmethylphosphinic acid chloride.

760 g of 2-carboxyethylmethylphosphinic acid were added portionswise to the molten reaction product while stirring and slowly heating to 110° C whereby a considerable formation of HCl took place. The addition was terminated after 1 and a half hours, the reaction mixture was heated for 2 hours in a water jet vacuum to 150° C. The contents of the flask were then submitted to a distillation in vacuo under 1 torr, 1253 g of colorless 2-methyl-2,5-dioxo-1,2-oxa-phospholane were obtained crystallizing when cooling.

Yield: 94% of the theory.

EXAMPLE 2

Preparation of 2-methyl-2,5-dioxo-1,2-oxa-phospholane from methyldichlorophosphine, Acrylic Acid and Water 1170 g (9.92 mols) of methyldichlorophosphine containing 0.8% of $PCl_3$ were introduced into a 2 liter flask provided with the device indicated in Example 1, and reacted with 755 g (10.5 mols) of acrylic acid in the manner described in Example 1 to yield 2-carboxyethyl-methylphosphinic acid dichloride.

185 g (10.3 mols) of water were then added dropwise to said dichloride while stirring, at a temperature from 60° to 85° C, within a period of 1 and a half hours, whereby a considerable HCl current escaped. After having terminated the addition the contents of the flask were heated to 95° C and drawn off by means of a water-jet vacuum pump until a vacuum of 20 torrs HCl was attained. THe colorless viscous residue (1654 g) was slowly heated to 180° C in vacuo, whereby HCl escaped once more. 2-Methyl-2,5-dioxo-1,2-oxa-phospholane distilled as a colorless liquid under a vacuum of about 1 torr, crystallizing at about 100° C. (Boiling point from 164° to 202° C at 1 torr).

Yield: 1180 g = 88.7% of the theory.

EXAMPLE 3

Preparation of 2-methyl-2,5-dioxo-1,2-oxa-phospholane from Methyldichlorophosphine, Acrylic Acid and Water In a 2 liter flask equipped as in Example 1 there were intorduced 1170 g (9.92 mols) of methyldichlorophosphine containing 0.8% of $PCl_3$ and reacted with 755 g (10.5 mols) of acrylic acid as described in Example 1 to yield 2-carboxyethylmethylphosphinic acid dichloride.

185 g (10.3 mols) of water were vaporized in a heated recipient (flask) within 1 and a half hours and incorporated into the above molten dichloride while stirring, in a vaporous state, with 3 l/h of nitrogen. The temperature of the contents of the flask raised from 60° to 118° C. A considerable HCl current escaped. HCl was then drawn off under a water-jet vacuum, whereby the temperature fell to less than 100° C.

The colorless viscous residue (1546 g) was slowly heated to 180° C in vacuo. 2-Methyl-2,5-dioxo-1,2-oxa-phospholane (boiling point from 175° to 211° C at 1 torr) distilled as colorless liquid under about 1 torr, crystallizing at about 100° C.

Yield: 1188 g = 89.5% of the theory.

EXAMPLE 4

Preparation of 2-methyl-2,5-dioxo-1,2-oxa-phospholane from Methyldichlorophosphine, Acrylic Acid and Water To 250 g (1.32 mols) of 2-chloroformylethylmethyl-phosphinic acid chloride which had been prepared from 155 g of methyldichlorophosphine and 95 g of acrylic acid there were added dropwise, while vigorously stirring, at a temperature from 25° to 45° C and cooling, 23.8 ml of water. Then the contents were heated to 75° C whereby a considerable formation of hydrogen chloride took place. Then the residual quantity of hydrogen chloride was removed at about 150° C in a water-jet vaccum. The residue was distilled under 0.2 torr. 173 g (98% of the theory) of 2-methyl-2,5-dioxo-1,2-oxa-phospholane were obtained.

EXAMPLE 5

Preparation of 2,4-dimethyl-2,5-dioxo-1,2-oxa-phospholane from Methyldichlorophosphine, Methacrylic Acid and Water 86 g (1 mol) of methacrylic acid were added dropwise to 117 g (1 mol) of methyldichlorophosphine at a temperature from 40° to 45° C. The mixture was stirred for 1 hour at said temperature. Phosphinic-carboxylic acid dichloride was then decomposed with 18 ml of $H_2O$ at a temperature of from 40° to 60° C, whereby a considerable formation of hydrogen chloride occurred. The residual quantity of hydrogen chloride in the reaction mixture was removed in a water-jet vacuum at 150° C. The residue was distilled under reduced pressure. 126 g of 2,4-dimethyl-2,5-dioxo-1,2-oxa-phospholane were obtained, which corresponds to a yield of 85.1% of the theory.

EXAMPLE 6

2-Phenyl-2,5-dioxo-1,2-oxa-phospholane 72 g (1 mol) of acrylic acid were added dropwise to 179 g (1 mol) of phenyldichlorophosphine at a temperature fron 60° to 80° C. After having terminated the addition the mixture was stirred for 1 hour at 70° C. The contents were then decomposed with 18 ml of $H_2O$; whereby a considerable formation of hydrogen chloride occurred. The residual quantities of hydrogen chloride were removed in a water-jet vacuum at a temperature of from 160° to 180° C. 184 g (94% of the theory) of 2-phenyl-2,5-dioxo1,2-oxa-phospholane were obtained melting at a temperature of from about 66° to 71° C after recrystallization from an acetone/ether mixture[Lit: melting point from 55° to 57° C, (Cf. A.N. Pudovnik et al., Z. obsc. Chim. 37, 455 (1967)].

What is claimed is:

1. Process for preparing 2,5-dioxo-1,2-phospholanes of the formula (I)

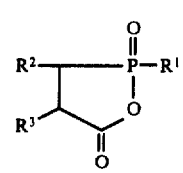

(I)

wherein $R^1$ represents an alkyl radical, optionally halogen substituted, having up to 18 carbon atoms, a cycloalkyl radical having up to 8 carbon atoms, an alkenyl radical having up to 8 carbon atoms, an aryl radical having up to 14 carbon atoms which may be substituted by lower alkyl groups having up to 4 carbon atoms, lower alkoxy groups having up to 4 carbon atoms, halogen or by amino groups alkylated or dialkylated by lower alkyl groups having up to 4 carbon atoms or an aralkyl radical having up to 15 carbon atoms which may be substituted in an analogous manner as the aryl radical, R² represents an alkyl radical having up to 4 carbon atoms or hydrogen and R³ represents an alkyl radical having up to 6 carbon atoms, a phenyl radical or a phenyl radical substituted by halogen or lower alkyl groups having up to 4 carbon atoms, a benzyl radical or hydrogen, which comprises reacting 2-halogeno-formylethylphosphinic acid halides of the formula (II)

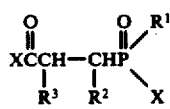
(II)

wherein R¹, R² and R³ are defined as in formula (I) and X represents chlorine or bromine, with approximately an equimolar quantity of water or a phosphinic-carboxylic acid of the formula (III)

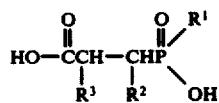
(III)

2. Process as claimed in claim 1, wherein at least one of the radicals R² and R³ represents a hydrogen atom.

3. Process as claimed in claim 1, wherein R¹ represents an alkyl radical having from 1 to 4 carbon atoms or an alkyl radical having from 1 to 4 carbon atoms substituted by halogen, cyclopentyl, cyclohexyl, vinyl, allyl, phenyl or phenyl substituted by lower alkyl groups having up to 4 carbon atoms, lower alkoxy groups having up to 4 carbon atoms, halogen or amino groups alkylated or dialkylated by lower alkyl groups having up to 4 carbon atoms or benzyl.

4. Process as claimed in claim 1, wherein R² represents methyl.

5. Process as claimed in claim 1, wherein R³ represents methyl.

6. Process as claimed in claim 1, wherein one of the radicals R² and R³ represents hydrogen and the other hydrogen or methyl.

7. Process as claimed in claim 1, which comprises carrying out the reaction at a temperature in the range of from −20° to +200° C.

8. Process as claimed in claim 1, comprises carrying out the reaction at a temperature in the range of from 0° to 160° C.

9. Process as claimed in claim 1, which comprises carrying out the reaction in the presence of solvents.

10. Process as claimed in claim 1, which comprises removing hydrogen halide from the reaction mixture by passing an inert gas through.

11. Process as claimed in claim 1, which comprises catching hydrogen halides formed by means of an acid acceptor.

* * * * *